United States Patent
Kalender et al.

(10) Patent No.: US 7,945,019 B2
(45) Date of Patent: May 17, 2011

(54) METHOD AND DEVICE FOR THERMAL BREAST TUMOR TREATMENT WITH 3D MONITORING FUNCTION

(75) Inventors: Willi Kalender, Moehrendorf (DE); Harry Schilling, Eichstaett (DE)

(73) Assignee: MIR Medical Imaging Research Holding GmbH, Moehrerdorf (DE)

( * ) Notice: Subject to any disclaimer, the term of this patent is extended or adjusted under 35 U.S.C. 154(b) by 0 days.

(21) Appl. No.: 12/402,225

(22) Filed: Mar. 11, 2009

(65) Prior Publication Data

US 2010/0080350 A1 Apr. 1, 2010

(30) Foreign Application Priority Data

Sep. 29, 2008 (DE) .......................... 10 2008 042 430

(51) Int. Cl.
G01N 23/04 (2006.01)
G01N 23/083 (2006.01)
H05G 1/60 (2006.01)

(52) U.S. Cl. ............ 378/62; 378/37; 378/65; 378/98.12

(58) Field of Classification Search .................... 378/37, 378/56, 62, 65, 98.12; 600/427
See application file for complete search history.

(56) References Cited

U.S. PATENT DOCUMENTS

| | | | |
|---|---|---|---|
| 3,673,394 A * | 6/1972 | Hartmann | 702/172 |
| 4,015,836 A | 4/1977 | Redington et al. | |
| 4,400,827 A * | 8/1983 | Spears | 378/207 |
| 4,680,028 A | 7/1987 | Stuart | |
| 4,709,382 A | 11/1987 | Sones | |
| 5,273,435 A | 12/1993 | Jacobson | |
| 5,308,321 A | 5/1994 | Castro | |
| 5,386,447 A | 1/1995 | Siczek | |
| 5,426,685 A | 6/1995 | Pellegrino et al. | |
| 5,528,043 A | 6/1996 | Spivey et al. | |
| 5,569,266 A | 10/1996 | Siczek | |
| 5,609,827 A | 3/1997 | Russell et al. | |
| 5,664,569 A | 9/1997 | Damadian et al. | |
| 5,757,878 A | 5/1998 | Dobbs et al. | |
| 5,803,912 A | 9/1998 | Siczek et al. | |

(Continued)

FOREIGN PATENT DOCUMENTS

DE 19639975 5/1998

(Continued)

OTHER PUBLICATIONS

"Laser interstitial thermotherapy (LITT) monitoring using high-resolution digital mammography: theory and experimental studies." Ahmed M Minhaj, et al., Phys. Med. Biol. 47 (2002) 2987-2999.*

(Continued)

*Primary Examiner* — Edward J Glick
*Assistant Examiner* — Thomas R Artman
(74) *Attorney, Agent, or Firm* — Kevin L. Daffer; Daffer McDaniel, LLP

(57) ABSTRACT

An X-ray machine for monitoring thermal treatment of human tissue produces a reference exposure of the tissue to be treated prior to commencement of the treatment. Thermal treatment is performed subsequently. Check exposures are made with the X-ray machine during the treatment or also during treatment intervals. The check exposures are performed as partial volume exposures at a lower radiation load than the reference exposures. From a comparison of check exposures with the reference exposures, conclusions can be drawn concerning changes of tissue temperature and also tissue properties.

15 Claims, 2 Drawing Sheets

U.S. PATENT DOCUMENTS

| | | | |
|---|---|---|---|
| 6,242,743 B1 | 6/2001 | DeVito et al. | |
| 6,298,114 B1 | 10/2001 | Yoda | |
| 6,325,537 B1 | 12/2001 | Watanabe | |
| 6,358,246 B1 | 3/2002 | Behl et al. | |
| 6,415,012 B1 | 7/2002 | Taguchi et al. | |
| 6,418,188 B1 | 7/2002 | Broadnax | |
| 6,419,390 B1 | 7/2002 | Landis-Lowell | |
| 6,463,122 B1 | 10/2002 | Moore | |
| 6,480,565 B1 | 11/2002 | Ning | |
| 6,684,097 B1* | 1/2004 | Parel et al. | 600/427 |
| 6,819,736 B1 | 11/2004 | Bruder et al. | |
| 6,837,772 B1 | 1/2005 | Luk | |
| 6,872,001 B1 | 3/2005 | Gilevich | |
| 7,005,988 B2 | 2/2006 | Mathewson, II et al. | |
| 7,065,393 B2 | 6/2006 | Sati et al. | |
| 7,304,578 B1 | 12/2007 | Sayers et al. | |
| 7,453,978 B1 | 11/2008 | DiBianca et al. | |
| 7,467,892 B2* | 12/2008 | Lang et al. | 378/207 |
| 7,492,858 B2 | 2/2009 | Partain et al. | |
| 7,556,426 B2 | 7/2009 | Nakajo et al. | |
| 7,558,370 B2 | 7/2009 | Sommer, Jr. et al. | |
| 7,677,799 B2 | 3/2010 | Jensen et al. | |
| 7,697,660 B2* | 4/2010 | Ning | 378/37 |
| 7,743,953 B2 | 6/2010 | Okazaki et al. | |
| 7,764,765 B2 | 7/2010 | Ohta et al. | |
| 2002/0181651 A1 | 12/2002 | Shepherd et al. | |
| 2003/0072409 A1 | 4/2003 | Kaufhold et al. | |
| 2003/0204965 A1 | 11/2003 | Hennessey | |
| 2004/0066880 A1 | 4/2004 | Oikawa | |
| 2004/0082856 A1 | 4/2004 | Marmarelis | |
| 2004/0092826 A1 | 5/2004 | Corbeil et al. | |
| 2004/0238750 A1 | 12/2004 | Vafi et al. | |
| 2004/0251419 A1 | 12/2004 | Nelson et al. | |
| 2004/0254461 A1 | 12/2004 | Ackerman, III | |
| 2005/0070817 A1 | 3/2005 | Mueller, Jr. | |
| 2006/0094950 A1 | 5/2006 | Ning | |
| 2006/0145871 A1 | 7/2006 | Donati et al. | |
| 2006/0262898 A1 | 11/2006 | Partain et al. | |
| 2007/0009080 A1* | 1/2007 | Mistretta | 378/4 |
| 2007/0064867 A1 | 3/2007 | Hansen et al. | |
| 2007/0092059 A1 | 4/2007 | Eberhard et al. | |
| 2007/0237306 A1 | 10/2007 | Jones et al. | |
| 2007/0238957 A1 | 10/2007 | Yared | |
| 2008/0033420 A1* | 2/2008 | Nields et al. | 606/27 |
| 2008/0037703 A1 | 2/2008 | Ting | |
| 2008/0081984 A1 | 4/2008 | Lafferty | |
| 2008/0084961 A1 | 4/2008 | Keppel et al. | |
| 2008/0089471 A1 | 4/2008 | Kobayashi | |
| 2008/0101538 A1 | 5/2008 | Schliermann | |
| 2008/0187095 A1 | 8/2008 | Boone et al. | |
| 2008/0205588 A1 | 8/2008 | Kim | |
| 2008/0221443 A1 | 9/2008 | Ritchie et al. | |
| 2008/0221478 A1 | 9/2008 | Ritchie et al. | |
| 2008/0230074 A1 | 9/2008 | Zheng et al. | |
| 2009/0080604 A1* | 3/2009 | Shores et al. | 378/37 |
| 2009/0196393 A1* | 8/2009 | Wang et al. | 378/4 |
| 2010/0080343 A1 | 4/2010 | Kalender | |
| 2010/0080344 A1 | 4/2010 | Schilling et al. | |
| 2010/0080345 A1 | 4/2010 | Schilling et al. | |
| 2010/0080346 A1 | 4/2010 | Kalender et al. | |
| 2010/0080347 A1 | 4/2010 | Kalender et al. | |
| 2010/0080348 A1 | 4/2010 | Kalender et al. | |
| 2010/0080349 A1 | 4/2010 | Kalender et al. | |
| 2010/0128843 A1 | 5/2010 | Tita | |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Mun et al., "Active RFID System Augmented with 2D Barcode for Asset Management in a Hospital Setting," IEEE International Conference on RFID, Mar. 2007, pp. 205-211.

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isotherm mapping in hyperthermia using subtraction X-ray computed tomography," Radiotherapy and Oncology, vol. 2, 1984, pp. 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Nov. 3, 2009 for U.S. Appl. No. 12/401,765.
Notice of Allowance mailed Apr. 15, 2010 for U.S. Appl. No. 12/401,765.
Office Action mailed Apr. 14, 2010 for U.S. Appl. No. 12/402,059.
Office Action mailed Apr. 1, 2010 for U.S. Appl. No. 12/402,141.
Notice of Allowance mailed Dec. 14, 2010 for U.S. Appl. No. 12/401,735.
Office Action mailed May 11, 2010 for U.S. Appl. No. 12/401,814.
Notice of Allowance mailed Aug. 23, 2010 for U.S. Appl. No. 12/401,765.
Notice of Allowance mailed Sep. 17, 2010 for U.S. Appl. No. 12/402,059.
Office Action mailed Sep. 23, 2010 for U.S. Appl. No. 12/401,792.
Notice of Allowance mailed Sep. 29, 2010 for U.S. Appl. No. 12/401,814.
Office Action mailed Jun. 10, 2010 for U.S. Appl. No. 12/401,735.
Office Action mailed Jun. 16, 2010 for U.S. Appl. No. 12/401,906.

* cited by examiner

METHOD AND DEVICE FOR THERMAL BREAST TUMOR TREATMENT WITH 3D MONITORING FUNCTION

PRIORITY CLAIM

This application claims priority to pending German Application No. 102008042430.7 filed on Sep. 29, 2008.

BACKGROUND OF THE INVENTION

1. Field of the Invention

This invention relates to an X-ray machine and also to a method for monitoring a diathermy treatment. In particular, the invention relates to an X-ray machine for imaging a breast of a female patient (mammography), and also a method for monitoring diathermy treatment of a breast tumor.

2. Description of Related Art

Various X-ray machines are used for performing an examination of a female breast. One type of X-ray machine comprises a rotating gantry, having an X-ray tube and an X-ray detector, located below a patient's table on which a patient to be examined rests. An embodiment of such an X-ray machine is disclosed, for example, in U.S. Pat. No. 4,015,836. The X-ray machine disclosed in U.S. Pat. No. 4,015,836 facilitates diagnosis of diseases of the breast, in particular, of tumors in the breast. The tumors detected by the X-ray machine may be treated in various ways. A proven treatment method is that of hyperthermy. In this treatment method, tissue in a vicinity of the tumor is heated so strongly that the cells of the tumor die away.

An embodiment of a hyperthermy instrument is disclosed in U.S. Pat. No. 6,358,246. An electrode of the hyperthermy instrument is introduced into the tumor to treat the tumor. Once inserted, the electrode is used to pass a high-frequency current through the tissue of the tumor. A rise of electrical impedance of the tissue is made use of here as a measure of maximum power. However, heating of the tumor cannot be controlled in a precise manner, because the temperature of the tissue is not directly related to the current flow or the energy introduced into the tissue by the electrode. Controlled therapy of a tumor is, therefore, difficult with an instrument of this kind.

U.S. Pat. No. 6,684,097 discloses a method for temperature monitoring during diathermy treatment of a breast. This method produces and stores a high-resolution three-dimensional X-ray exposure or photograph of a breast before treatment. During the treatment, further high-resolution three-dimensional photographs of the breast are produced and compared with the original exposure. The method compares the exposures taken before and during treatment, and from a difference between individual pixel values, draws conclusions about a temperature change. A disadvantage of this method is the high radiation load caused during the high-resolution three-dimensional exposures.

BRIEF SUMMARY OF THE INVENTION

The following description of the objective of the disclosure provided herein and the description of embodiments of an X-ray machine, medical instruments for treating tumors and methods for monitoring and controlling such a medical instrument is not to be construed in any way as limiting the subject matter of the appended claims.

An objective of the disclosure provided herein is to provide a method for at least one of monitoring and controlling a medical instrument, in particular, for monitoring or controlling diathermal tumor treatment of a female breast. In the methods disclosed herein, the radiation load is substantially reduced from the loads that typically occur during a three-dimensional X-ray scan.

Another objective of the disclosure is to provide a medical instrument with which a thermal tumor treatment and, in particular, controlled diathermal tumor treatment of a female breast can be performed, with the radiation load being substantially reduced from the loads that typically occur during a three-dimensional X-ray scan.

An embodiment of a method for monitoring an instrument for thermal treatment of body tissue of a particular region of a human body comprises: producing at least one reference exposure of a region to be treated with an X-ray machine; performing a thermal treatment on the region; producing at least one check exposure of the region with the X-ray machine; and producing at least one temperature change profile by comparing the at least one check exposure with the at least one reference exposure. In one embodiment, the at least one check exposure is produced as a partial volume exposure of the region to be treated, using a lower radiation dose than that typically used for three-dimensional X-ray exposures.

An X-ray machine adapted for performing the above method is also provided herein, along with a system for controlled thermal treatment of body tissue. In addition to the X-ray machine, the system comprises an instrument coupled to the X-ray machine for at least one of heating and cooling a certain region of the body tissue.

BRIEF DESCRIPTION OF THE DRAWINGS

In the following the invention is described by way of example, without limitation of the general inventive concept, on examples of embodiment and with reference to the drawings.

Figure 1:
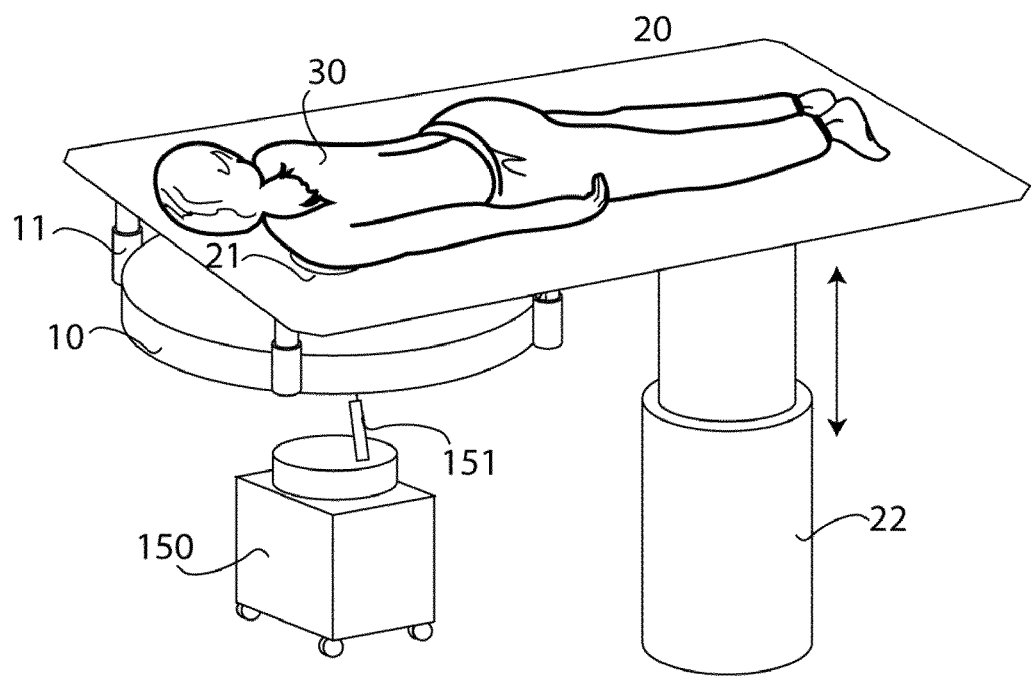
FIG. 1 shows an embodiment of an X-ray machine for examining and/or treating a breast of a female patient.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

FIG. 1 illustrates an embodiment of an X-ray machine for examining and/or treating a female breast. A patient 30 rests on a support surface, which in the illustrated embodiment, is a patient's table 20. Although illustrated as having a horizontally disposed support surface 20 for the patient, it is also possible for the support surface disclosed herein to be disposed vertically, or at other angles of inclination.

The breast to be examined is inserted through a breast cutout portion 21 in the patient's table 20 into an exposure range of a gantry 10. The gantry 10 shown in FIG. 1 is a spiral computer tomograph (CT) gantry having an X-ray tube and an X-ray detector (not shown in FIG. 1), which rotate around the breast to be examined. The breast is imaged with X-rays during rotation of the gantry 10. Simultaneously with the rotation, a displacement of the gantry along a vertical direction is performed via a gantry lift drive 11, so that the breast is scanned with X-rays along a spiral-shaped trajectory. In one embodiment, the height of the patient's table 20 can be adjusted via a patient's table lift drive 22. As described in more detail below, a diathermy appliance 150 is provided for supplying energy to the patient's breast with an instrument 151, which results in heating of a region of interest in the breast.

A method is provided herein for monitoring an instrument (e.g., the diathermy instrument 150, 151 of FIG. 1) used for thermal treatment of a body tissue located in a particular region of a human body. In one embodiment, the method may begin by producing an X-ray exposure of a region to be treated. At least one reference X-ray exposure is made of the tissue to be treated. In some embodiments, a multitude of reference X-ray exposures may be made of the tissue to be treated.

In one embodiment, the reference exposure(s) are followed by a diathermy treatment, which generally involves heating the tissue to be treated. A new treatment can be begun, or a previous treatment continued. To heat the tissue, energy is coupled into the tissue via a medical instrument (e.g., instrument 151 of FIG. 1). The energy is preferably in the form of electrical energy, but may also be in the form of irradiation. In other embodiments, the medical instrument may be adapted for cooling, instead of heating, the tissue to be treated. Heating or cooling of the tissue can be effected by: (i) an electric current, preferably a high-frequency current; (ii) focused ultrasound; (iii) heat radiation, preferably in the far-infrared; (iv) terahertz radiation; (v) a heating and/or cooling medium such as a liquid or a gas, with a liquefied gas (e.g., liquid nitrogen) being preferred; or (vi) a combination of one or more of the above.

For monitoring the diathermy treatment, X-ray exposures are preferably taken at various intervals during the treatment and compared with the reference exposure(s) taken before treatment began. In one embodiment, a simple subtraction of brightness values may be performed to compare the X-ray exposures taken before and during treatment. Differences between the X-ray exposures taken during treatment and the reference exposure(s) may indicate a temperature change within the tissue. The temperature change can be used to monitor the operation of the diathermy instrument.

In general, the X-ray exposures obtained during treatment (referred to herein as "check exposures") can be taken at various intervals or during short intervals of treatment. In addition, the check exposures are made with a total radiation dose that is lower than the radiation dose typically expected from a normal high resolution three-dimensional exposure. Furthermore, the check exposures may be performed as a partial volume exposure, in which only a certain region of tissue selected for temperature monitoring is irradiated and imaged.

X-ray examinations have shown that with diathermy treatment, i.e., with a temperature change of the tissue, the X-ray properties change by a few Hounsfield units. The underlying physical effect is presumably that of a density change of the tissue.

With the method described herein, it is now possible to establish a temperature profile of a thermally treated region. With use of 3D X-ray machines, a spatial temperature profile can also be established. The use of a temperature profile enables the course of treatment to be precisely monitored. For example, the instrument producing the temperature change can be suitably set and/or regulated during treatment based on the temperature profile obtained during treatment. In addition, treatment can be terminated once a certain temperature profile is attained. The method described herein enables the radiation dose to be kept relatively low, since embodiments of the method may only require a partial volume exposure to be made of the heated region. Furthermore, the instrument causing a temperature change, or a sensor of this instrument, can be positioned precisely within the tissue prior to commencement of a treatment, and also during the treatment.

Figure 2:
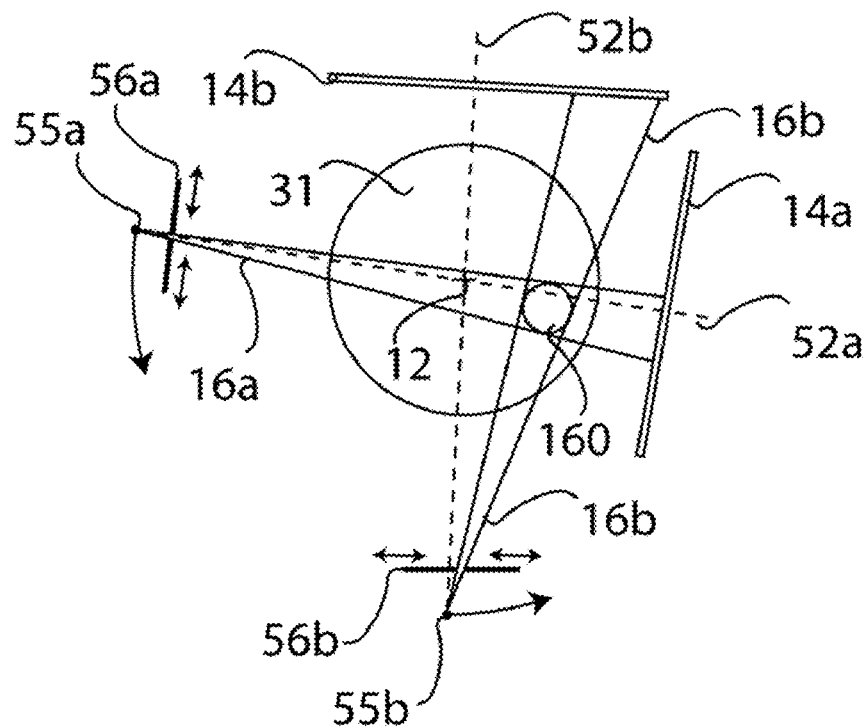
FIG. 2 illustrates how an X-ray beam generated by the X-ray machine may be dynamically collimated.

FIG. 2 illustrates an embodiment of a dynamic focusing method for minimizing radiation load on the patient during a temperature measurement. Instead of performing a complete highly resolving 3D scan during temperature measurement, radiation loads are minimized by taking multiple exposures from multiple directions. In the embodiment of FIG. 2, an exposure is taken from each of two positions or directions displaced by an angle of 90° from each other. An arrangement of this kind is generally adequate for determining a temperature distribution with sufficient accuracy. This is based on a realization that in approximately homogeneous materials, such as human body tissue, the temperature distribution developed within the tissue is spherical to a first approximation.

Figure 3:
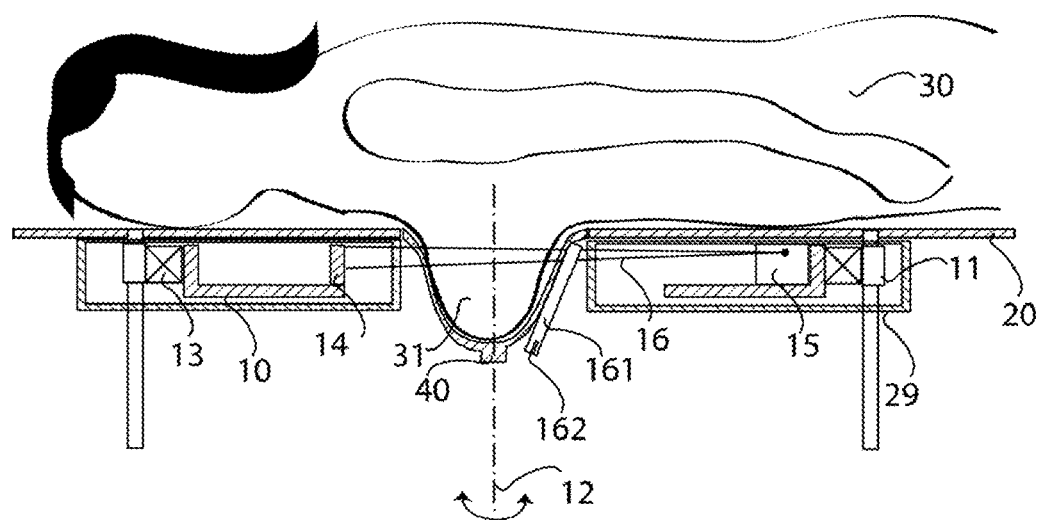
FIG. 3 shows a lateral view of a longitudinal cross-section through the X-ray shown in FIG. 1.

FIG. 2 illustrates one embodiment of how the X-ray tube 15 and X-ray detector shown, e.g., in FIG. 3 may be moved to obtain multiple exposures at multiple locations. The reference numerals shown in FIG. 2 are indicative of position. For example, a reference numeral followed by the letter 'a' corresponds to a first position, whereas a reference numeral followed by the letter 'b' corresponds to a second position of the X-ray tube and detector.

A first exposure is made with X-rays starting from a first position of the X-ray tube having a first focal point or spot 55*a*. An aperture 56*a* positioned in front of the spot 55*a* is suitably adjusted to produce an X-ray fan beam 16*a*, which is just large enough to cover a range of interest (ROI) 160 within the tissue to be examined with as little radiation as possible being emitted into the surrounding tissues. The radiation emitted from the X-ray tube and passed through the range of interest 160 is intercepted with an X-ray detector in the position 14*a* and evaluated. As shown in FIG. 2, the central ray 52*a* associated with the first position of the X-ray tube and X-ray detector may lie within the bounds of the X-ray fan 16*a*. The X-ray tube and X-ray detector are moved to the second position to provide a second focal point 55*b* and detector position 14*b*. The aperture 56*b* is suitably adjusted to produce an X-ray fan 16*b*, which also comprises the region of interest (ROI) 160 as exactly as possible. The radiation emitted from the X-ray tube and passed through the region of interest is detected by the detector in the position 14*b* and evaluated. In this position, the central ray 52*b* lies outside of the X-ray fan 16*b*.

FIG. 3 shows a side view of a cross-section through an X-ray machine used for examining a breast of a female patient. The cross-section is taken through a gantry 10 of the X-ray machine. The gantry 10 comprises an X-ray tube 15, which generates an X-ray fan beam 16 for penetrating the breast 31. In the embodiment of FIG. 3, the breast 31 is fixed in a locating device 40 situated within a gantry housing 29. The radiation emitted from the X-ray tube 15 and passed through the breast 31 is received by a detector 14 and evaluated by an evaluation unit (not shown in FIG. 3). The gantry 10 is rotatably supported by a gantry pivot bearing 13. The bearing 13 enables the gantry to be rotated about a rotational axis 12 of the gantry 10 and around the breast 31. In addition, the gantry 10 is adapted to be displaced vertically by means of a gantry lift drive 11. A scan of the breast 31 is obtained along a spiral-shaped trajectory by rotating the gantry 10 around the breast, while vertically displacing the gantry during the rotation.

In one embodiment, the gantry 10 rotates continuously during a thermal treatment and completes temperature measurements at predetermined intervals of time. In one embodiment, temperature measurements may be performed by taking multiple exposures from multiple angular directions. For example, and as shown in FIG. 2, temperature measurements may be performed by taking check exposures from each of two positions or angles, which are displaced by an angle of 90° relative to each other. Of course, the X-ray tube may be excited only for performing temperature measurements or taking exposures.

In one embodiment, it may be sufficient to perform temperature measurements at relatively long intervals of time, for example, 1, 5, 10, 20 or 60 seconds. For shorter intervals of time, the gantry can rotate relatively slowly. For longer intervals of time, such as 10, 20 or 60 seconds, the gantry preferably rotates at a speed which enables the gantry to complete several revolutions within the designated time interval, so that a time lag between two measurements made at positions displaced from each other by 90° is reduced. By way of example, for measurement intervals of 60 seconds, one revolution per second is performed. In such an example, a time delay between two measurements made from positions displaced from each other by 90° is 0.25 seconds.

Although not illustrated in FIG. 3, the X-ray machine described herein permits check exposures to be made during thermal treatment of the tissue, because the gantry allows the diathermy instrument (not shown in FIG. 3) to pass through the gantry without impeding the movement of the gantry during scans along the spiral-shaped trajectory. During thermal treatment, it is of particular advantage for a plurality of exposures to be made during the circular or spiraling movement of the gantry 10, and for an aperture 56 to be set according to the movement so that the X-ray radiation from the X-ray tube covers only a predetermined region of the tissue under examination. The aperture may be adjusted in a stepwise or continuous manner following movement of the X-ray tube and detector.

In one embodiment, check exposures may be taken from two positions or angular directions displaced 90° from one another. As an alternative to taking exposures from positions displaced by 90°, a plurality of exposures can be made from various positions of the gantry 10. In this case, the aperture 56 is independently set for each of the various positions so that the X-ray radiation from the X-ray tube covers only a predetermined region of the tissue.

In one embodiment, the X-ray machine described herein is provided with at least one container having a reference medium or a reference fluid 161 disposed therein. Examples of suitable reference fluids include, but are not limited to, water and glycerol. A temperature sensor 162 is also provided for monitoring the temperature of the reference fluid.

The X-ray machine may be calibrated with the container containing the reference medium 161 and the temperature sensor 162. For example, changes of the X-ray properties of the tissue due to temperature changes within the tissue may be relatively small. In order to accurately determine temperature changes within the tissue, the X-ray machine can be calibrated in each case with the reference fluid, or in a general case with a reference medium. In one embodiment, the calibration may be performed before and/or during a reference exposure and/or a check exposure.

As noted above, the X-ray machine described herein comprises a support surface or table 20 for a patient 30, and also a gantry 10 with an X-ray tube and a detector which can be vertically displaced with respect to a patient by means of a Z axis drive. In addition, the X-ray machine offers access for an instrument to pass through the gantry for insertion into a tissue of the patient. The instrument may be configured for heating and/or cooling the tissue to be treated. Heating or cooling of the tissue can be effected by (i) an electric current, preferably a high-frequency current; (ii) focused ultrasound; (iii) heat radiation, preferably in the far-infrared; (iv) terahertz radiation; (v) a heating and/or cooling medium such as a liquid or a gas, with a liquefied gas (e.g., liquid nitrogen) being preferred; or (vi) a combination of one or more of the above.

Furthermore, the X-ray machine is provided with means for collimating the X-ray radiation from the X-ray tube. For producing exposures from a plurality of positions it is necessary to adjust the beam collimation independent of position. In one embodiment, beam collimation is adjusted by means of an aperture 56. The aperture preferably narrows the X-ray fan 16 to a plane perpendicular to the rotational axis 12 of the gantry 10. Alternatively, the aperture may narrow the X-ray fan beam 16 to a plane parallel to the rotational axis 12.

In one embodiment, methods and procedures for improving the temporal and/or spatial resolution of exposures may be used in combination with the various exposures. As the exposures differ from each other only by local parameters (such as, for example, the temperature in a certain sub-volume to be subjected to therapy), a temporal/spatial combination of exposures improves image quality, or alternatively, minimizes the radiation dose applied to a patient with image quality remaining unchanged. Examples of such methods include, but are not limited to, PICCS (prior image constrained compressed sensing) and HYPR (highly constrained back projection).

The X-ray machine described herein is preferably a CT scanner and has an adjustable aperture 56. Preferably at least one reference medium 161 is also provided.

A medical system in accordance with the invention for monitored diathermy treatment of body tissue comprises an X-ray machine as described above, and also an instrument for heating and/or cooling the body tissue. This may be, for example, a diathermy instrument or also an instrument for cryo-therapeutic treatment.

It will be appreciated to those skilled in the art having the benefit of this disclosure that this disclosure is believed to provide X-ray machines and methods for monitoring an instrument for thermal treatment of body tissue. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method for monitoring an instrument for thermal treatment of body tissue of a particular region of a human body, the method comprising:
   producing at least one reference exposure of a region to be treated with an X-ray machine;
   performing a thermal treatment on the region;

producing at least one check exposure of the region with the X-ray machine, wherein the at least one check exposure is produced as a partial volume exposure of the region, and wherein the step of producing the at least one check exposure provides a lower radiation dose than that used for the reference exposure by producing two exposures from two angular positions of a gantry having an X-ray tube and an X-ray detector and being adapted to rotate about the region being treated, wherein the two angular positions are displaced from each other by an angle of 90°; and producing at least one temperature-change profile by comparing the at least one check exposure with the at least one reference exposure.

2. The method according to claim 1, wherein before the at least one check exposure is produced, an aperture is set so that X-ray radiation from the X-ray machine covers only a predetermined region.

3. The method according to claim 1, wherein the step of producing the at least one check exposure comprises
setting an aperture for each of the two positions so that X-ray radiation from the X-ray machine covers only a predetermined region.

4. The method according to claim 1, wherein the method is combined with one or more methods for improving at least one of a temporal and spatial resolution selected from a group comprising prior image constrained compressed sensing (PICCS) and highly constrained back projection (HYPR).

5. The method according to claim 1, further comprising calibrating the X-ray machine prior to, or simultaneously with, the steps of performing a reference exposure or performing at least one check exposure, wherein the calibration step involves a comparison of an exposure performed on at least one reference medium.

6. The method according to claim 5, wherein the exposure performed on the at least one reference medium is performed along with at least one of the steps of performing a reference exposure and performing at least one check exposure.

7. The method according to claim 5, wherein the step of calibrating comprises measuring a temperature of the reference medium.

8. An X-ray machine for examining a breast of a female patient, the X-ray machine comprising:
a gantry that is rotatable about a rotational axis and simultaneously movable in a direction parallel to the rotational axis, and thus, covers a cylindrical imaging region, wherein the gantry comprises an X-ray tube for emitting a beam of radiation, an adjustable aperture for collimating the beam of radiation so that the radiation passes through a partial volume of the breast, and an X-ray detector for detecting the radiation emitted from the X-ray tube and passed through the partial volume of the breast;
a support surface on which the patient is positioned so that the breast to be imaged projects into the imaging region of the gantry;
wherein the gantry offers access for an instrument to pass through the gantry for insertion into the breast of the patient, and wherein the instrument is configured for heating and/or cooling tissue located within a region of the breast; and
wherein the adjustable aperture follows movement of the X-ray tube and the X-ray detector as the gantry rotates about the rotational axis, and wherein the adjustable aperture is independently set at various rotational positions of the gantry to ensure that the radiation passes only through the partial volume.

9. The X-ray machine according to claim 8, wherein the X-ray machine is a CT scanner.

10. The X-ray machine according to claim 8, wherein a reference medium is provided for calibration of the X-ray machine.

11. A system for controlled thermal treatment of body tissue, the system comprising:
an X-ray machine comprising:
a gantry that is rotatable about a rotational axis and simultaneously movable in a direction parallel to the rotational axis, and thus, covers a cylindrical imaging region; and
a support surface on which the patient is positioned so that the body tissue to be imaged projects into the imaging region of the gantry;
wherein the gantry comprises an X-ray tube for emitting a beam of radiation, an adjustable aperture for collimating the beam of radiation so that the radiation passes through a partial volume of the body tissue, and an X-ray detector for detecting the radiation emitted from the X-ray tube and passed through the partial volume of the body tissue;
wherein the adjustable aperture follows movement of the X-ray tube and the X-ray detector as the gantry rotates about the rotational axis, and wherein the adjustable aperture is independently set at various rotational positions of the gantry to ensure that the radiation passes only through the partial volume; and
an instrument coupled to the X-ray machine for at least one of heating and cooling a particular region of the body tissue.

12. The system according to claim 11, wherein the gantry provides access for the instrument to pass through the gantry for insertion into the body tissue.

13. The system according to claim 11, wherein a reference medium is provided for calibration of the X-ray machine.

14. A method for monitoring an instrument for thermal treatment of body tissue of a particular region of a human body, the method comprising:
producing at least one reference exposure of a region to be treated with an X-ray machine;
performing a thermal treatment on the region;
producing at least one check exposure of the region with the X-ray machine, wherein the at least one check exposure is produced as a partial volume exposure of the region, and wherein the step of producing the at least one check exposure provides a lower radiation dose than that used for the reference exposure by setting the aperture so that X-ray radiation from the X-ray machine covers only a predetermined region; and
producing at least one temperature-change profile by comparing the at least one check exposure with the at least one reference exposure.

15. A method for monitoring an instrument for thermal treatment of body tissue of a particular region of a human body, the method comprising:
producing at least one reference exposure of a region to be treated with an X-ray machine;
performing a thermal treatment on the region;
producing at least one check exposure of a partial volume of the region with the X-ray machine, wherein the at least one, check exposure is produced as a partial volume exposure of the region, and wherein the step of producing the at least one check exposure provides a lower radiation dose than that used for the reference exposure; and
producing at least one temperature-change profile by comparing the at least one check exposure with the at least one reference exposure.

* * * * *